(12) United States Patent
Velarde et al.

(10) Patent No.: US 8,367,877 B2
(45) Date of Patent: Feb. 5, 2013

(54) METHODS OF PURIFYING 1,2,4-BUTANETRIOL

(75) Inventors: Stephen P. Velarde, Christiansburg, VA (US); Andrew J. Sanderson, Blacksburg, VA (US)

(73) Assignee: Alliant Techsystems Inc., Arlington, VA (US)

( * ) Notice: Subject to any disclaimer, the term of this patent is extended or adjusted under 35 U.S.C. 154(b) by 676 days.

(21) Appl. No.: 12/620,131

(22) Filed: Nov. 17, 2009

(65) Prior Publication Data

US 2011/0118511 A1    May 19, 2011

(51) Int. Cl.
*C07C 29/80* (2006.01)
*C07C 31/22* (2006.01)
(52) U.S. Cl. ......... 568/868; 568/853; 568/864; 568/872
(58) Field of Classification Search .................. 568/868, 568/872, 853, 864
See application file for complete search history.

(56) References Cited

U.S. PATENT DOCUMENTS

| | | |
|---|---|---|
| 6,027,926 A | 2/2000 | Kawada et al. |
| 6,479,714 B1 | 11/2002 | Schofield et al. |
| 6,949,684 B2 | 9/2005 | Ikai et al. |
| 7,056,439 B2 | 6/2006 | Baniel et al. |

FOREIGN PATENT DOCUMENTS

| | | |
|---|---|---|
| EP | 0879893 A1 | 11/1998 |
| EP | 1553073 A1 | 7/2005 |

OTHER PUBLICATIONS

U.S. Appl. No. 11/445,910, filed Jun. 2, 2006.

*Primary Examiner* — Elvis O Price
(74) *Attorney, Agent, or Firm* — TraskBritt

(57) ABSTRACT

Methods of purifying BT are disclosed. The method comprises adding at least one polyhydroxyl compound to a crude BT mixture comprising BT and at least one boron-containing compound to form a polyhydroxyl compound/BT mixture. In one embodiment, the polyhydroxyl compound/BT mixture is then heated to a temperature greater than the boiling point of BT but less than the boiling point of the at least one polyhydroxyl compound. In another embodiment, the polyhydroxyl compound/BT mixture is heated to a temperature greater than the melting point of the at least one polyhydroxyl compound, and then to a temperature greater than the boiling point of BT but less than the boiling point of the at least one polyhydroxyl compound. A composition comprising BT is also disclosed.

18 Claims, 1 Drawing Sheet

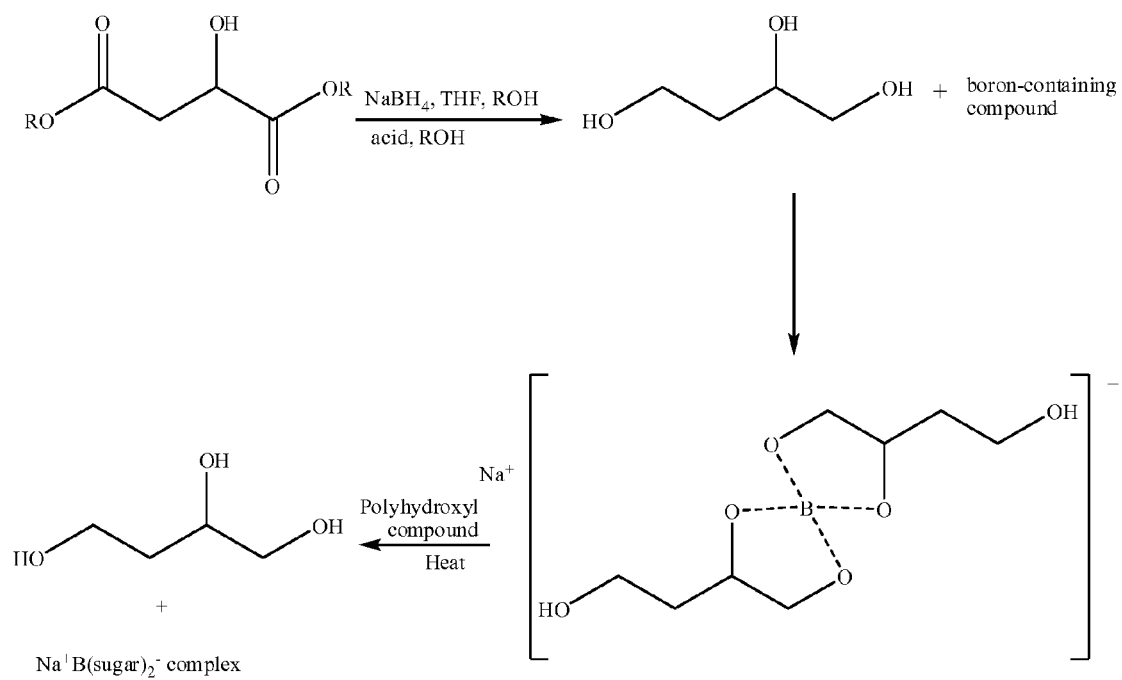

METHODS OF PURIFYING 1,2,4-BUTANETRIOL

TECHNICAL FIELD

Embodiments of the present invention relate to methods for isolating and purifying 1,2,4-butanetriol (BT). More specifically, embodiments of the present invention relate to methods of isolating and purifying BT using a polyhydroxyl compound. Embodiments of the present invention also relate to compositions including the BT.

BACKGROUND

BT is a precursor to butanetrioltrinitrate (BTTN), which is used as an energetic plasticizer in tactical rocket motor propellants, and some pharmaceutical compounds or agricultural chemicals. Multiple methods of synthesizing BT are known, such as the hydroformylation of glycidol and subsequent reduction of the reaction product, the catalytic hydrogenation of malic acid, and biotechnological syntheses using genetically engineered bacteria. Another method of synthesizing BT includes reducing a dialkyl malate with sodium borohydride. However, in addition to producing BT, the latter reaction produces borate salts as an impurity. The borate salts bind to the BT, forming a complex, which prevents the isolation of pure BT. To remove the borate salts, large volumes of an alcohol solvent are used in a distillation process. However, the distillation involves using large amounts of a flammable and toxic material (the alcohol solvent), and is labor intensive. While the BT obtained from the distillation has an organic purity of greater than 98%, the resulting BT includes inorganic impurities, such as the borate salts.

Ion exchange chromatography has been used to remove the borate salts. However, the boron-specific ion exchange resins do not have the capacity to remove large amounts of boron. In addition, the boron-specific ion exchange resins do not effectively remove the borate salts in the presence of a competitive binding agent, such as BT.

It would be desirable to be able to isolate and purify BT using a process capable of removing large quantities of borate salts using a relatively inexpensive and non-toxic starting material. The purified BT would be free of inorganic impurities.

BRIEF SUMMARY

An embodiment of the invention comprises a method of purifying BT. The method comprises adding at least one polyhydroxyl compound to a crude BT mixture comprising BT and at least one boron-containing compound to form a polyhydroxyl compound/BT mixture. The polyhydroxyl compound/BT mixture is then heated to a temperature greater than the boiling point of BT but less than the boiling point of the at least one polyhydroxyl compound.

Another embodiment of the invention comprises a composition comprising BT. The composition comprises the BT and substantially no boron. The BT in the composition is synthesized by reacting a dialkyl malate with sodium borohydride.

BRIEF DESCRIPTION OF THE DRAWING

While the specification concludes with claims particularly pointing out and distinctly claiming that which is regarded as the present invention, the advantages of this invention may be more readily ascertained from the following description of the invention when read in conjunction with the accompanying drawing in which:

FIG. 1 illustrates the reaction of a dialkyl malate with sodium borohydride to form BT, and the subsequent isolation and purification of pure BT.

DETAILED DESCRIPTION

A method of isolating and purifying BT is disclosed. The method includes adding at least one polyhydroxyl compound to a crude BT mixture. As used herein, the term "crude BT mixture" means and includes a mixture of BT, at least one boron-containing compound, and a complex thereof. The crude BT mixture may also include elemental boron. Once heated, the polyhydroxyl compound reacts with the boron-containing compound, enabling pure BT to be isolated from the crude BT mixture.

As used herein, the terms "comprising," "including," "containing," "characterized by," and grammatical equivalents thereof are inclusive or open-ended terms that do not exclude additional, unrecited elements or method steps, but also include the more restrictive terms "consisting of" and "consisting essentially of" and grammatical equivalents thereof. As used herein, the term "may" with respect to a material, structure, feature or method act indicates that such is contemplated for use in implementation of an embodiment of the invention and such teem is used in preference to the more restrictive term "is" so as to avoid any implication that other, compatible materials, structures, features and methods usable in combination therewith should, or must be, excluded.

The BT of the crude BT mixture may be produced by reacting a dialkyl malate with sodium borohydride, as shown in the reaction scheme of FIG. 1. In FIG. 1, R is an alkyl group, such as a methyl, ethyl, propyl, butyl, pentyl, hexyl, heptyl, or higher alkyl group. Sodium borohydride may also be reacted with other malate derivatives to produce the BT, such as malate derivatives where the R group is an alkoxy group (such as methoxy, ethoxy, propoxy, butoxy, pentoxy, hexoxy, or higher alkoxy), an aryloxy group (such as phenoxy), or a halogen (such as fluorine, chlorine, bromine, or iodine). By way of non-limiting example, the dialkyl malate may be dimethyl malate, such as dimethyl D-malate, dimethyl L-malate, or combinations thereof, which is commercially available from various suppliers, such as from Sigma-Aldrich Co. (St. Louis, Mo.). The dialkyl malate may be dissolved in an alcohol, and the dialkyl malate/alcohol solution added to a solution or suspension of sodium borohydride in THF or other suitable solvent. The alcohol may be an alkyl alcohol, such as methanol, ethanol, propan-1-ol, propan-2-ol, n-butanol, sec-butanol, tert-butanol and combinations thereof. The dialkyl malate/alcohol solution may be slowly added to the sodium borohydride/THF (or other suitable solvent) solution or suspension, with stirring, over a time period ranging from approximately two hours to approximately six hours. While the descriptions herein describe adding the dialkyl malate/alcohol solution to the sodium borohydride/THF solution or suspension, the order of combining the dialkyl malate/alcohol solution and the sodium borohydride/THF solution or suspension may be altered as long as the two become combined in a vessel, such as in a reaction vessel. During the combination, the contents of the vessel may be maintained at a temperature of less than or equal to the boiling point of the highest-boiling solvent used. By way of non-limiting example, the contents of the vessel may be maintained at a temperature of less than or equal to approximately 30° C., such as by using a water bath. The dialkyl malate may react with the sodium borohydride for from approximately one hour to approximately 24 hours at a temperature of from approximately −10° C. to approximately 70° C. The above-mentioned time and temperature ranges may be modified to achieve different yields of the BT. While various examples herein describe producing the BT by a process similar to that described above, the BT may be produced by other conventional techniques in which a boron-containing compound is produced as an impurity.

As the reaction proceeds to completion, the sodium borohydride is consumed, a homogeneous solution of BT is produced, and hydrogen is evolved. As used herein, the term "homogeneous" means the resulting solution has a uniform composition. The BT in the BT solution may include a racemic mixture of the two BT enantiomers. The BT solution has a greater viscosity than the viscosity of the dialkyl malate/alcohol solution and sodium borohydride/THF solution or suspension when initially combined. Since the viscosity of the BT solution increases as the BT is formed and since the reaction of the dialkyl malate and the sodium borohydride produces hydrogen, the contents of the vessel may be continually stirred or otherwise treated to control foaming.

After the reaction has proceeded to the desired extent or to completion, a solvent may be added to the BT solution to decrease its viscosity. The solvent may be an alcohol, such as methanol. An aqueous acid solution may then be added to quench the reaction and precipitate inorganic salts, such as sodium chloride or sodium borate, while the BT and boron-containing compound remain in solution. The inorganic salts may be filtered from the BT solution, producing the crude BT mixture, which includes BT, approximately 15% by weight of the boron-containing compound, and small quantities of the solvents (such as alcohol, water, and THF), reaction by-products, and unreacted dialkyl malate. The boron-containing compound may be dissolved in the crude BT mixture, which is a viscous liquid, along with the BT.

The boron-containing compound in the crude BT mixture may be a boron-containing salt, such as a borate salt. Elemental boron may also be present in the crude BT mixture. While removal of the boron-containing compound from the crude BT mixture is described in detail herein, elemental boron that is present in the crude BT mixture may be removed in a similar manner. If the boron-containing compound or elemental boron were to remain in the crude BT mixture, the boron-containing compound or elemental boron may bind strongly to compounds containing vicinal diol groups, such as BT, which contains three hydrophilic hydroxyl groups. Specifically, a boron atom of the boron-containing compound or the elemental boron may coordinate with the vicinal hydroxyl groups of two molecules of BT, forming a BT-borate complex, as shown in FIG. 1. The crude BT mixture may include the BT-borate complex as well as unreacted BT and boron-containing compound. Since the BT-borate complex is not volatile and the BT is bound to the boron-containing compound or elemental boron, isolating substantially pure BT from the crude BT mixture is substantially prevented.

To isolate the BT from the crude BT mixture, at least one polyhydroxyl compound may be added to the vessel containing the crude BT mixture, forming a polyhydroxyl compound/BT mixture. As explained in detail below, the polyhydroxyl compound/BT mixture may include the BT-borate complex and unreacted polyhydroxyl compound, or may include a polyhydroxyl compound/borate complex and free BT depending on the extent of reaction between the polyhydroxyl compound and the boron atom of the BT-borate complex. The polyhydroxyl compound/BT mixture may be heated to a temperature that is greater than the melting point of the polyhydroxyl compound but less than the boiling point of the polyhydroxyl compound. The heat may be applied to the polyhydroxyl compound/BT mixture by conventional techniques, such as by heating the vessel in which the polyhydroxyl compound/BT mixture is contained using a water bath or oil bath. The temperature to which the polyhydroxyl compound/BT mixture is heated may depend on the polyhydroxyl compound that is used. By way of non-limiting example, the polyhydroxyl compound/BT mixture may be heated to a temperature ranging from approximately 2° C. to approximately 20° C. greater than the melting point of the polyhydroxyl compound. The temperature of the polyhydroxyl compound/BT mixture may be gradually increased or increased in a stepwise manner until the temperature of the polyhydroxyl compound/BT mixture is greater than the melting point of the polyhydroxyl compound. As the polyhydroxyl compound melts, the polyhydroxyl compound/BT mixture may be stirred, forming a homogeneous solution that is flowable. As this solution is heated and stirred, the polyhydroxyl compound may react with the boron atom in the BT-borate complex, forming the polyhydroxyl compound/borate complex, which includes the polyhydroxyl compound bound to the boron atom of the boron-containing compound. The polyhydroxyl compound may function as a competitive binder of the boron-containing compound, displacing the BT from the BT-borate complex and forming the polyhydroxyl compound/borate complex. Once released from the BT-borate complex, the free BT may be easily separated from the polyhydroxyl compound/borate complex, as described below.

To react with the boron atom of the BT-borate complex, the polyhydroxyl compound may include at least two hydroxyl groups that are vicinal relative to one another. The polyhydroxyl compound may be cyclic or linear. The polyhydroxyl compound may have a melting point within a range of from approximately 90° C. to approximately 120° C., and a boiling point within a range of from approximately 170° C. to approximately 200° C. To enable subsequent removal of the BT from the polyhydroxyl compound/borate complex, the polyhydroxyl compound may be less volatile (have a higher boiling point) than the BT. BT has a reported boiling point of from approximately 160° C. to approximately 190° C. For example, at 18 torr, the boiling point of BT is 190° C. to 191° C. The boiling point of the polyhydroxyl compound may be at least approximately 10° C. greater than the boiling point of BT.

By way of non-limiting example, the polyhydroxyl compound may be a non-reducing sugar having a melting point lower than the temperature at which the BT is removed from the polyhydroxyl compound/BT mixture and a boiling point higher than the boiling point of BT. In addition, the polyhydroxyl compound may be substantially non-toxic and relatively low cost. As used herein, the term "non-reducing sugar" means and includes a monosaccharide or a disaccharide that is not capable of chemically reducing certain oxidizing agents, such as Tollen's reagent, Benedict's reagent, or Fehling's reagent. These reagents are known in the art and, therefore, the components of the reagents are not discussed in detail herein. The polyhydroxyl compound may also be a polysaccharide or an oligosaccharide. The non-reducing sugar may contain at least five carbon atoms, such as a pentose (five carbon atoms), a hexose (six carbon atoms), or a heptose (seven carbon atoms). The non-reducing sugar may include, but is not limited to, mannitol, sorbitol, erythritol, xylitol, fructose, allose, raffinose, or combinations thereof. Either D- or L-forms of the non-reducing sugar may be used as the polyhydroxyl compound. The non-reducing sugar may have a purity of greater than approximately 98%, such as a food grade, non-reducing sugar. Such non-reducing sugars are commercially available from numerous sources.

The polyhydroxyl compound may be added to the crude BT mixture at from approximately 0.5 molar equivalent to approximately 2 molar equivalents of the polyhydroxyl compound relative to the amount of boron-containing compound. To enable the boron-containing compound to most efficiently react with the polyhydroxyl compound, at least approximately 1 molar equivalent of the polyhydroxyl compound may be added to the crude BT mixture. The boron atom of the BT-borate complex may coordinate with the vicinal hydroxyl groups of the polyhydroxyl compound, producing the polyhydroxyl compound/borate complex and free BT. If unreacted boron-containing compound is present in the crude BT mixture, the boron atom of the boron-containing compound may coordinate with the vicinal hydroxyl groups of the polyhydroxyl compound, forming the polyhydroxyl compound/borate complex and enabling the BT to remain unbound. Since the polyhydroxyl compound binds more strongly to the boron-containing compound than the BT binds to the boron-containing compound, the polyhydroxyl compound/borate complex may be more thermodynamically stable than the BT-borate complex.

The free or unbound BT, which is more volatile (has a lower boiling point) than the polyhydroxyl compound/borate complex, may be isolated and purified from the polyhydroxyl compound/BT mixture, such as by distillation. After the polyhydroxyl compound melts and sufficient time has elapsed for the polyhydroxyl compound to react with the boron atom of the BT-borate complex or unreacted boron-containing compound, the polyhydroxyl compound/BT mixture may be heated to a temperature greater than the boiling point of BT but less than the boiling point of the polyhydroxyl compound. The temperature of the polyhydroxyl compound/BT mixture may be gradually increased or increased in a stepwise manner to raise the temperature of the polyhydroxyl compound/BT mixture to a temperature greater than the boiling point of the BT. By way of non-limiting example, if the polyhydroxyl compound is mannitol or sorbitol, the polyhydroxyl compound/BT mixture may be heated to a temperature ranging from approximately 180° C. to approximately 250° C. to distill the BT from the polyhydroxyl compound/borate complex. Heating the polyhydroxyl compound/BT mixture to a temperature within this range produces a sufficient temperature at the head of the condenser for the BT to be distilled from the polyhydroxyl compound/BT mixture. Since there is typically a 50° C. to 60° C. difference between the temperature of the polyhydroxyl compound/BT mixture as heated in the vessel and the temperature at the head of the condenser, heating the polyhydroxyl compound/BT mixture to a temperature of from approximately 180° C. to approximately 250° C. is sufficient to enable the BT to be distilled from the polyhydroxyl compound/borate complex. The polyhydroxyl compound/BT mixture may be heated under reduced pressure to improve the distillation of the BT. For instance, the pressure in the vessel that contains the polyhydroxyl compound/BT mixture may be reduced to and maintained at from approximately 2 mm Hg to approximately 20 mm Hg before heating the polyhydroxyl compound/BT mixture. The BT distilled from the polyhydroxyl compound/BT mixture may be collected and stored for use. The remaining polyhydroxyl compound/borate complex is a non-hazardous glassy material that may be disposed of.

While the process of purifying the BT described above includes heating the polyhydroxyl compound/BT mixture to a first temperature to dissolve the polyhydroxyl compound, and then heating the polyhydroxyl compound/BT mixture to a second temperature greater than the boiling point of BT, the polyhydroxyl compound/BT mixture may be heated to a temperature greater than the boiling point of BT in a single act such that the polyhydroxyl compound dissolves and the BT is subsequently removed.

The BT removed from the polyhydroxyl compound/BT mixture may be a clear, colorless to pale-yellow liquid. The BT may have a similar viscosity to glycerine. The BT produced as described above may have a higher total purity than the BT produced by conventional techniques in that the BT may be substantially free of boron (such as the boron-containing compound or elemental boron) or other inorganic impurities. For instance, no elemental boron or boron-containing compounds may be detected in the resulting BT, as measured by Inductively Coupled Plasma/Mass Spectroscopy (ICP/MS). The BT may have a total purity (organic and inorganic purity) of greater than approximately 98%. Organic impurities remaining in the BT may include reaction by-products, such as 3-hydroxybutyrolactone and hydroxytetrahydrofuran. The yield of the BT produced as described above may be approximately 75% based on the amount of dialkyl malate.

In addition to the high purity that is achieved, the BT produced as described above may be advantageous because large amounts of expensive, flammable, and toxic solvents are not needed to purify and isolate the BT. Rather, the BT produced as described above utilizes an inexpensive polyhydroxyl compound. Since the process described above is capable of removing substantially all of the boron, the process described above may remove greater amounts of the boron-containing compound than chromatographic techniques conventionally used to remove the boron-containing compound.

The following examples serve to explain embodiments of the present invention in more detail. These examples are not to be construed as being exhaustive or exclusive as to the scope of this invention.

EXAMPLES

Example 1

Preparation of Crude BT Mixture

A crude BT mixture was prepared by dissolving (1 kg, 6.17 mol) of dimethyl malate in 1 L of methanol. Granular sodium borohydride (466 g, 12.3 mol) was suspended in 3.2 L of THF (GC grade, stabilized with 250 ppm BHT) in a 10 L, jacketed reactor with an overhead paddle-type stirrer. A slow nitrogen purge was maintained over the sodium borohydride suspension. The dimethyl malate/methanol solution was added to the sodium borohydride suspension over a four-hour time period, while maintaining the reaction temperature at less than or equal to approximately 30° C. with a recirculating cold water bath. Mild gassing was observed over the course of the addition and during the ensuing reaction. The reaction mixture was stirred at 25° C. to 30° C. for 16 hours. As the reaction progressed, the sodium borohydride granules were consumed and the reaction mixture became a homogeneous solution. However, the reaction mixture became increasingly viscous. The increased viscosity resulted in foaming of the reaction mixture, as hydrogen is slowly evolved during the reaction. The reaction mixture was continually stirred to control the foaming.

To reduce the viscosity, 500 ml of methanol was added to the reaction mixture, followed by the addition of 1 L of a methanolic hydrochloric acid solution (37% aqueous HCl in 1 L methanol) to quench the reaction. Mild gassing was observed during the initial stage of the quench process, and the temperature was maintained below 35° C. A heavy white precipitate formed, and the mixture was stirred for one hour. At this point, the pH of the reaction mixture was between 6 and 8. The reaction mixture was filtered, and precipitated sodium salts (sodium chloride and sodium borate) were washed with three 500 ml portions of methanol. The solvent was removed from the combined filtrates by evaporating the solvent under reduced pressure (rotovap bath temperature 40° C. to 45° C.) to concentrate the crude BT. Additional salts precipitated during the concentration, and were filtered.

The crude BT mixture obtained after the concentration was a viscous, clear, pale-yellow liquid. The mass of the crude BT mixture corresponded to greater than 100% yield and included BT, dissolved borate species, and solvent. The organic purity of the crude BT mixture, as measured by gas chromatography (GC), was greater than 98%. The organic purity refers to the purity of organic species in the crude BT mixture but does not include inorganic species. Since the organic purity of the crude BT mixture only accounts for organic species, the crude BT mixture was not substantially pure because the boron content of the crude BT mixture was 11%-16% by weight, as determined by inductively coupled plasma (ICP) analysis.

As necessary, the crude BT mixture was passed through a thin bed (100 g-150 g) of AMBERLITE® IRN-78 ion-exchange resin. The resin was washed with methanol to recover additional crude BT. At this point, the crude BT mixture had a pH of between 7 and 8. To prevent the BT from cyclizing, the pH of the crude BT mixture is maintained between 6 and 10. The neutralized, crude BT mixture was concentrated on a rotovap (bath temperature 90° C. to 95° C.) to constant weight. The boron content of the crude BT mixture, as determined by ICP analysis, was 2% by weight to 3% by weight. The mass of the crude BT mixture was 85 g to 95 g. At 3% boron, the crude BT mixture included between 2.6 g and 2.8 g (0.24 mol-0.26 mol) of boron.

Example 2

Purification of BT Using D-Sorbitol

The crude BT mixture (97 g), produced as described in Example 1, was contained in a 500-ml round-bottom flask. The crude BT mixture included BT and 3% by weight of boron. D-sorbitol (117.3 grams) was added to the round-bottom flask and the contents of the round-bottom flask were heated under vacuum with stirring. The contents were heated using an oil bath under mild vacuum to melt the D-sorbitol. At a temperature greater than approximately 110° C., the D-sorbitol melted, forming a homogeneous solution of the D-sorbitol and BT. Once homogeneity was achieved, the temperature of the oil bath was gradually increased to between 190° C. and 230° C. and the vacuum was increased to distill the BT. A small quantity of low-boiling liquid was initially collected (residual solvent, trimethyl borate, and 3-hydroxytetrahydrofuran) through a short-path distillation head. This fraction was discarded. The temperature of the oil bath was maintained between 190° C. and 230° C., and BT was collected through a short-path distillation head (head distillation temperature was between 120° C. and 130° C.).

The BT was distilled as a clear, viscous, colorless to pale-yellow liquid. The average yield of BT isolated by this process was 59.6% (based on dimethyl malate). From 1 kg of dimethyl malate, at least 390 g of pure BT was recovered. The highest pure BT yield from this process was 78% (72.3 g pure BT from 97 g crude BT mixture (including approximately 4% by weight boron)).

Example 3

Purification of BT Using D-Mannitol

The crude BT mixture (93.4 g), produced as described in Example 1, was placed in a distillation flask. The boron content of the crude BT mixture was approximately 4% by weight, which corresponded to 3.73 g (0.346 mol) of boron. D-mannitol (136.5 grams, 0.695 mol) was added to the crude BT mixture, which corresponded to a 2:1 D-mannitol:boron ratio. The crude BT mixture was heated under vacuum with stirring to a temperature between 200° C. and 230° C. The D-mannitol gradually melted and the mixture became a homogeneous solution. Water (4.5 g) was recovered as a low boiling fraction and discarded. BT (76.7 g) was recovered from the crude BT mixture, which corresponded to a 98% recovery of BT from the boron-contaminated material.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the scope of the invention as defined by the following appended claims and their legal equivalents.

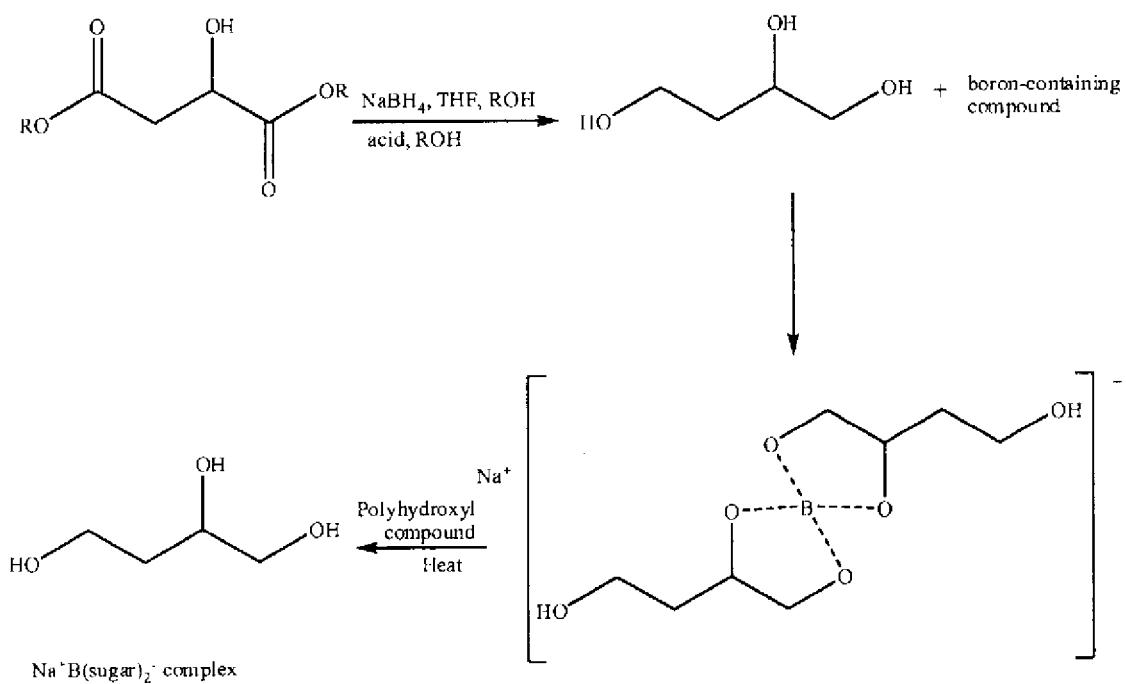

What is claimed is:

1. A method of purifying 1,2,4-butanetriol, comprising:
   adding at least one polyhydroxyl compound to a crude 1,2,4-butanetriol mixture comprising 1,2,4-butanetriol and at least one boron-containing compound to form a polyhydroxyl compound/1,2,4-butanetriol mixture; and
   heating the polyhydroxyl compound/1,2,4-butanetriol mixture to a temperature greater than the boiling point of 1,2,4-butanetriol but less than the boiling point of the at least one polyhydroxyl compound.

2. The method of claim 1, wherein adding at least one polyhydroxyl compound to a crude 1,2,4-butanetriol mixture comprising 1,2,4-butanetriol and at least one boron-containing compound to form a polyhydroxyl compound/1,2,4-butanetriol mixture comprises adding at least one polyhydroxyl compound comprising at least two vicinal hydroxyl groups to the crude 1,2,4-butanetriol mixture.

3. The method of claim 1, wherein adding at least one polyhydroxyl compound to a crude 1,2,4-butanetriol mixture comprising 1,2,4-butanetriol and at least one boron-containing compound to form a polyhydroxyl compound/1,2,4-butanetriol mixture comprises adding at least one polyhydroxyl compound having a melting point within a range of from approximately 90° C. to approximately 120° C. to the crude 1,2,4-butanetriol mixture.

4. The method of claim 1, wherein adding at least one polyhydroxyl compound to a crude 1,2,4-butanetriol mixture comprising 1,2,4-butanetriol and at least one boron-containing compound to form a polyhydroxyl compound/1,2,4-butanetriol mixture comprises adding at least one polyhydroxyl compound having a boiling point within a range of from approximately 170° C. to approximately 200° C. to the crude 1,2,4-butanetriol mixture.

5. The method of claim 1, wherein adding at least one polyhydroxyl compound to a crude 1,2,4-butanetriol mixture comprising 1,2,4-butanetriol and at least one boron-containing compound to form a polyhydroxyl compound/1,2,4-butanetriol mixture comprises adding the at least one polyhydroxyl compound having a boiling point at least approximately 10° C. greater than the boiling point of 1,2,4-butanetriol to the crude 1,2,4-butanetriol mixture.

6. The method of claim 1, wherein adding at least one polyhydroxyl compound to a crude 1,2,4-butanetriol mixture comprising 1,2,4-butanetriol and at least one boron-containing compound to form a polyhydroxyl compound/1,2,4-butanetriol mixture comprises adding at least one non-reducing sugar to the crude 1,2,4-butanetriol mixture.

7. The method of claim 1, wherein adding at least one polyhydroxyl compound to a crude 1,2,4-butanetriol mixture comprising 1,2,4-butanetriol and at least one boron-containing compound to form a polyhydroxyl compound/1,2,4-butanetriol mixture comprises adding at least one of a monosaccharide, a disaccharide, a polysaccharide, an oligosaccharide, or combinations thereof to the crude 1,2,4-butanetriol mixture.

8. The method of claim 1, wherein adding at least one polyhydroxyl compound to a crude 1,2,4-butanetriol mixture comprising 1,2,4-butanetriol and at least one boron-containing compound to form a polyhydroxyl compound/1,2,4-butanetriol mixture comprises adding mannitol, sorbitol, erythritol, xylitol, fructose, allose, raffinose, or combinations thereof to the crude 1,2,4-butanetriol mixture.

9. The method of claim 1, wherein adding at least one polyhydroxyl compound to a crude 1,2,4-butanetriol mixture comprising 1,2,4-butanetriol and at least one boron-containing compound to form a polyhydroxyl compound/1,2,4-butanetriol mixture comprises adding from approximately 0.5 molar equivalent to approximately 2 molar equivalents of the at least one polyhydroxyl compound relative to the at least one boron-containing compound to the crude 1,2,4-butanetriol mixture.

10. The method of claim 1, wherein heating the at least one polyhydroxyl compound/1,2,4-butanetriol mixture to a temperature greater than the boiling point of 1,2,4-butanetriol but less than the boiling point of the at least one polyhydroxyl compound comprises reacting the at least one polyhydroxyl compound and the at least one boron-containing compound to form a polyhydroxyl compound-borate complex.

11. The method of claim 1, wherein heating the at least one polyhydroxyl compound/1,2,4-butanetriol mixture to a temperature greater than the boiling point of 1,2,4-butanetriol but less than the boiling point of the at least one polyhydroxyl compound comprises heating the polyhydroxyl compound/1,2,4-butanetriol mixture to a temperature of from approximately 180° C. to approximately 250° C.

12. The method of claim 1, wherein heating the at least one polyhydroxyl compound/1,2,4-butanetriol mixture to a temperature greater than the boiling point of 1,2,4-butanetriol but less than the boiling point of the at least one polyhydroxyl compound comprises heating the polyhydroxyl compound/1,2,4-butanetriol mixture to a temperature of from approximately 190° C. to approximately 230° C.

13. The method of claim 1, wherein heating the at least one polyhydroxyl compound/1,2,4-butanetriol mixture to a temperature greater than the boiling point of 1,2,4-butanetriol but less than the boiling point of the at least one polyhydroxyl compound comprises stepwise heating of the polyhydroxyl compound/1,2,4-butanetriol mixture to a temperature greater than the boiling point of 1,2,4-butanetriol but less than the boiling point of the at least one polyhydroxyl compound.

14. The method of claim 1, wherein heating the at least one polyhydroxyl compound/1,2,4-butanetriol mixture to a temperature greater than the boiling point of 1,2,4-butanetriol but less than the boiling point of the at least one polyhydroxyl compound comprises gradual heating of the polyhydroxyl compound/1,2,4-butanetriol mixture to a temperature greater than the boiling point of 1,2,4-butanetriol but less than the boiling point of the at least one polyhydroxyl compound.

15. The method of claim 1, further comprising distilling the 1,2,4-butanetriol from the polyhydroxyl compound/1,2,4-butanetriol mixture.

16. A method of purifying 1,2,4-butanetriol, comprising:
adding a polyhydroxyl compound to a crude 1,2,4-butanetriol mixture comprising 1,2,4-butanetriol and at least one boron-containing compound to form a polyhydroxyl compound/1,2,4-butanetriol mixture;
heating the polyhydroxyl compound/1,2,4-butanetriol mixture to a temperature greater than the melting point of the polyhydroxyl compound to form a polyhydroxyl compound/1,2,4-butanetriol solution; and
heating the polyhydroxyl compound/1,2,4-butanetriol solution to a temperature greater than the boiling point of 1,2,4-butanetriol but less than the boiling point of the polyhydroxyl compound.

17. The method of claim 16, further comprising distilling the 1,2,4-butanetriol from the polyhydroxyl compound/1,2,4-butanetriol solution.

18. The method of claim 16, wherein adding a polyhydroxyl compound to a crude 1,2,4-butanetriol mixture comprising 1,2,4-butanetriol and at least one boron-containing compound to form a polyhydroxyl compound/1,2,4-butanetriol mixture comprises adding the polyhydroxyl compound to the crude 1,2,4-butanetriol mixture further comprising elemental boron.

* * * * *

UNITED STATES PATENT AND TRADEMARK OFFICE
CERTIFICATE OF CORRECTION

PATENT NO. : 8,367,877 B2
APPLICATION NO. : 12/620131
DATED : February 5, 2013
INVENTOR(S) : Stephen P. Velarde et al.

It is certified that error appears in the above-identified patent and that said Letters Patent is hereby corrected as shown below:

In the drawings:
    Please replace Fig. 1 with Fig. 1 as shown on the attached page.
    In FIG. 1, change "$Na^1B(sugar)_2^-$ complex" to
    --$Na^+B(sugar)_2^-$ complex--

In the specification:
    COLUMN 7, LINE 28, change "IRN-78" to --IRN78--

Signed and Sealed this
Sixth Day of May, 2014

Michelle K. Lee
*Deputy Director of the United States Patent and Trademark Office*